United States Patent [19]

Stametz et al.

[11] Patent Number: 5,601,475

[45] Date of Patent: Feb. 11, 1997

[54] METHOD OF MANUFACTURING SURGICAL NEEDLES HAVING BLUNT TIPS

[75] Inventors: Jerry W. Stametz, Freemonsburg, Pa.; William C. McJames, Belle Meade, N.J.

[73] Assignee: Ethicon, Inc., Somerville, N.J.

[21] Appl. No.: 664,896

[22] Filed: Jun. 17, 1996

Related U.S. Application Data

[63] Continuation of Ser. No. 280,911, Jul. 27, 1994, abandoned.

[51] Int. Cl.⁶ .................................................. B24B 31/033
[52] U.S. Cl. ............................ 451/35; 451/36; 451/327; 451/329; 451/330
[58] Field of Search ............................ 451/32, 33, 34, 451/35, 326, 327, 328, 329, 330, 36; 606/223, 222

[56] References Cited

U.S. PATENT DOCUMENTS

| 2,407,642 | 9/1946 | Ashworth . | |
|---|---|---|---|
| 3,680,266 | 8/1972 | Shiplov | 451/32 |
| 4,011,691 | 3/1977 | Grund | 451/33 |
| 4,110,085 | 8/1978 | Balz | 451/32 |
| 4,581,855 | 4/1986 | Kato et al. . | |
| 4,905,357 | 3/1990 | Fenlon . | |
| 5,123,910 | 6/1992 | McIntosh | 606/223 |
| 5,383,901 | 1/1995 | McGregor et al. | 606/223 |
| 5,447,465 | 9/1995 | Samsel et al. | 451/32 |

FOREIGN PATENT DOCUMENTS

06444019A1 7/1994 European Pat. Off. .

*Primary Examiner*—Timothy V. Eley
*Attorney, Agent, or Firm*—Emil Richard Skula

[57] ABSTRACT

A method of manufacturing blunt tip surgical needles. Taper point needles having conventional piercing tips are placed into a vessel containing a grinding media. The needles are maintained in the vessel for a sufficient amount of time to convert the piercing point into a blunt tip.

34 Claims, 3 Drawing Sheets

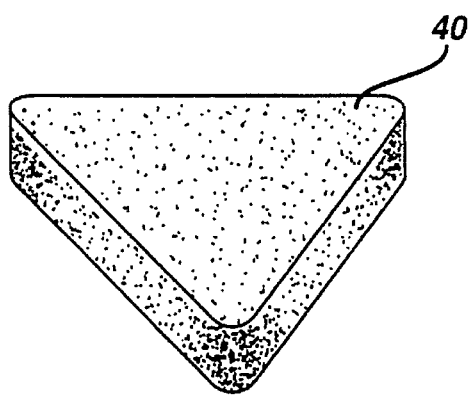
FIG. 3A
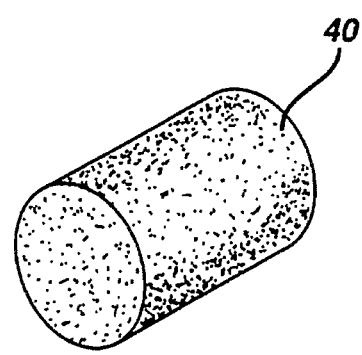
FIG. 3B
FIG. 3C
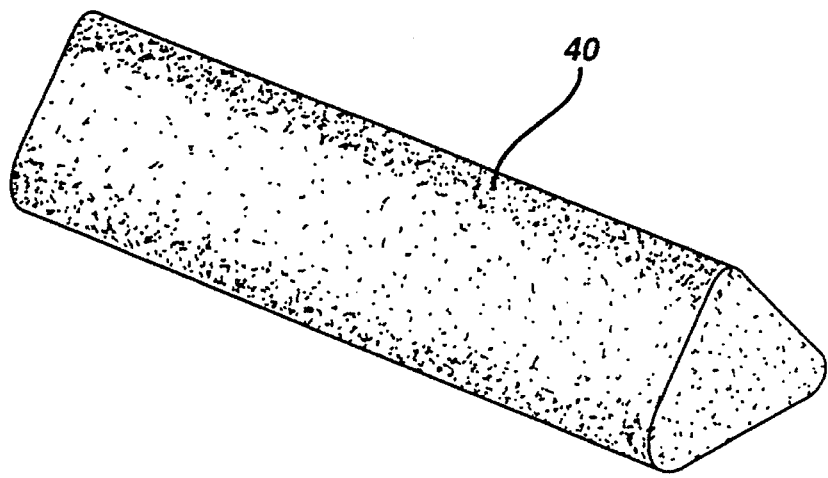

FIG. 7 _PRIOR ART_

METHOD OF MANUFACTURING SURGICAL NEEDLES HAVING BLUNT TIPS

This is a continuation of application Ser. No. 08/280,911, filed Jul. 27, 1994 now abandoned.

TECHNICAL FIELD

The field of art to which this invention pertains is surgical needles, more specifically taper point surgical needles having blunt tips.

BACKGROUND OF THE INVENTION

Blunt tip needles have been found to be effective tools in the on-going battle to control the spread of infectious agents borne in body fluids when used in a generally recognized control program including the use of double gloves, appropriate protective clothing and face shields, appropriate needle packaging, and special packing and disposal techniques for used needles. It is widely known that bacterial and viral diseases such as H.I.V., hepatitis, various venereal disease, etc., can be spread through contact with the body fluids of infected individuals. The Occupational Health & Safety Agency (O.S.H.A.) has recently promulgated regulations governing the exposure of workers to infectious agents. The regulations are concerned, in part, with the transmission of infectious agents by puncture wounds or cuts from various sharp medical devices which have been contaminated with body fluids potentially containing infectious agents, e.g., hypodermic needles, catheters, etc.

It is known that a surgeon during the course of a major operation may sustain one or more needle sticks when suturing with a surgical needle. In addition, support personnel are also exposed to potential needle sticks when handling surgical needles having sharp piercing points.

Blunt tip surgical needles were developed over thirty years ago for use on certain friable tissue such as the kidney. More recently, their use to prevent needle sticks as part of a multi-faceted program to prevent the spread of infectious agents has become accepted in the medical field. The blunt tip needles of prior art, however, were known to have problems penetrating through tough tissues and could only be used on certain types of soft tissues.

As previously mentioned, there is a heightened concern regarding the spread of infectious diseases caused by contact with infectious body fluids. Consequently, the medical community has now demanded that surgical needle manufacturers supply blunt tip needles useful in many types of tissue (in addition to friable tissue) as part of their infectious disease control programs. In order to provide blunt tip taper point needles which approach the penetration characteristics of conventional taper point needles (having sharp piercing tips) and which have utility on various types of tissue, it has been necessary to decrease the radius of the points of blunt tip needles. However, it is known that such blunt tip needles having improved tissue piercing characteristics are difficult to manufacture compared to conventional blunt tip needles which are designed for use with friable tissue.

Blunt tip surgical needles are conventionally manufactured using a lathe-type process. In such a process, a conventional wire is cut into blanks which are fed into a lathe machine. A tool spins or orbits about the distal end of each wire blank to form a blunt end or tip having a desired profile. However, it is known that conventional blunt tip manufacturing processes have several deficiencies. A major deficiency relates to dimensional instability. This is believed to be caused, at least in part, by the cutting tools wearing out rapidly. This condition worsens when cutting blunt tip needles having smaller tip radii. Two cutting tools are conventionally used in a blunt tip needle manufacturing process. One tool forms the proximal section of the taper, and one tool forms the distal, blunt profile, piercing tip. It is possible for the two cutting tools to be out of synchronization resulting in the manufacture of needles having out of specification needle and tip profiles. Yet another deficiency associated with conventional blunt tip manufacturing processes relates to the limitation on the types of alloys which can be processed with conventional cutting tools. In particular, it is known that hard alloys wear out cutting tools very quickly. Still yet another deficiency associated with existing blunt tip manufacturing processes is the slow throughput of machinery used in such processes when compared with conventional sharp taper point needle manufacturing processes.

Therefore, what is needed in this art is a process for manufacturing blunt tip needles which is efficient and economical, which reduces dimensional variability, which can be readily used on a multitude of alloys, and which eliminates the need for cutting tools to produce blunt tips.

DISCLOSURE OF THE INVENTION

Accordingly, it is an object of the present invention to provide a novel process for manufacturing blunt point surgical needles.

It is a further object of the present invention to provide a process for the manufacture of blunt tip surgical needles in which the dimensions of the blunt tips can be precisely monitored and controlled in a reproducible manner.

It is yet a further object of the present invention to provide a method of manufacturing blunt tip needles having tip configurations which cannot be readily made using conventional manufacturing processes.

It is still yet a further object of the present invention to provide a process for manufacturing blunt tip needles having improved efficiency.

Yet another object of the present invention is to provide a process for manufacturing blunt tip needles which can be used on a wide variety of alloys.

Still yet another object of the present invention is a process for manufacturing blunt tip needles which eliminates the need for conventional cutting tools to produce a blunt tip.

Accordingly, a novel process for manufacturing blunt tip surgical needles is disclosed. The process comprises the steps of initially placing surgical needles having conventional, sharp taper points, or if desired, semi-finished taper needle blanks with truncated tips, into an apparatus having a vessel which is capable of displacement, preferably rotation, wherein the vessel contains an abrasive or grinding media. The vessel is then displaced, e.g., rotated, to cause the abrasive or grinding media to contact the needles for a sufficient amount of time to effectively convert the taper points, or truncated points, to blunt tips having a desired configuration.

Yet another aspect of the present invention is a blunt tip surgical needle manufactured by the previously-described method.

Other features and advantages of the invention will become more apparent from the following description and accompanying drawings.

BRIEF DESCRIPTION OF THE DRAWINGS

FIG. 3A is a perspective view of a grinding media useful in the process of the present invention having a triangular shape.

FIG. 3B is a perspective view of a grinding media useful in the process of the present invention having a cylindrical shape.

FIG. 3C is a perspective view of a grinding media useful in the practice of the present invention having a triangular cross-section.

FIG. 7 is a perspective view of a conventional blunt tip needle.

BEST MODE FOR CARRYING OUT THE INVENTION

Surgical needles typically consist of an elongated shaft having a proximal suture mounting portion and a distal piercing point. Surgical needles are typically classified as either taper-point needles, wherein the diameter of the shaft tapers to a piercing point, or cutting edge needles, wherein the needles have various cutting edges along with a piercing point to assist in penetrating various types of tissue. A conventional process for manufacturing a taper point needle having a sharp piercing point typically consists of initially cutting wire into needle blanks. Each needle blank is then subjected to a series of grinding operations. These operations may be conventionally performed in the following manner. The needle blanks are fed into a conventional belt/stone grinding machine where they are given a sharp distal piercing tip. The needles are then transported individually or in bulk to a conventional needle drilling station wherein the needles are drilled using conventional carbide or tool steel drill bits to provide a proximal suture mounting cavity. If desired, the mounting cavity may be laser drilled. The needles are then typically degreased and moved in bulk to a conventional belt/stone grinding machine for a finish taper grind and then to a curving machine to produce a conventional curved configuration. The needles are then cleaned, heat treated and may be electrochemically treated to additionally finish the needles.

Blunt tip needles are conventionally made in a similar manner. However, rather than grinding the distal tip, a lathe type process is used instead to produce a blunt tip having a desired blunt profile.

The term "taper point" as used herein is defined to mean the distal end of a surgical needle having a taper profile which tapers from a maximum dimension to a distal minimum, wherein the distal point forms a piercing point.

The terms "abrasive" and "grinding" are used interchangeably herein and are defined to describe the process of mechanically removing metal from a part or object by contacting the part or object with a media. A grinding or abrasive media is defined to mean a composition or a plurality of objects, particularly shaped objects, which will cause the mechanical removal of material from a part or object when forcibly contacted therewith.

Figure 1:
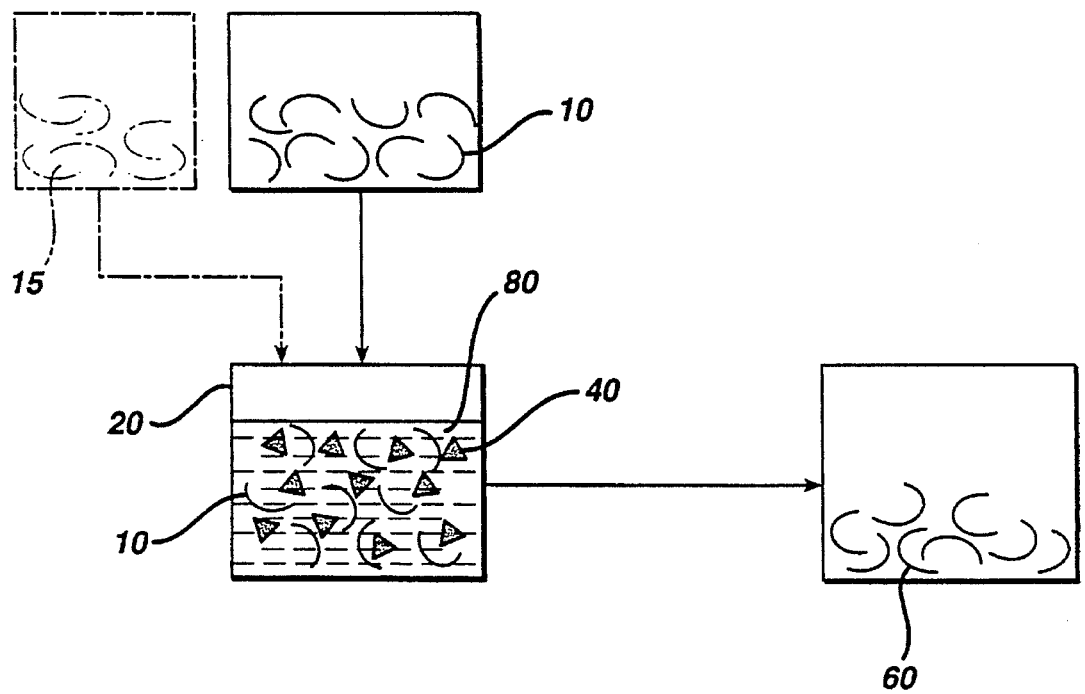
FIG. 1 is a flow diagram of a blunt tip manufacturing process of the present invention.
Figure 4:
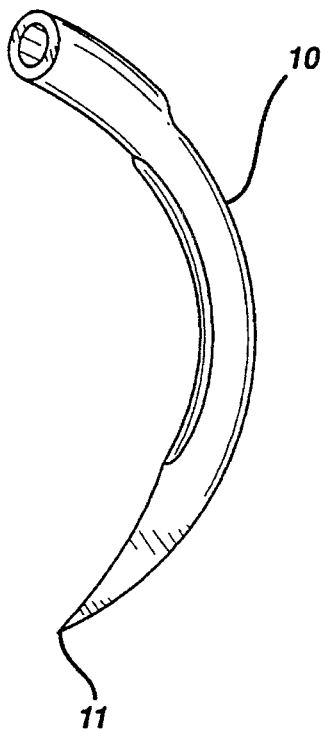
FIG. 4 is a perspective view of a taper point needle having a conventional, sharp piercing point.
Figure 5:
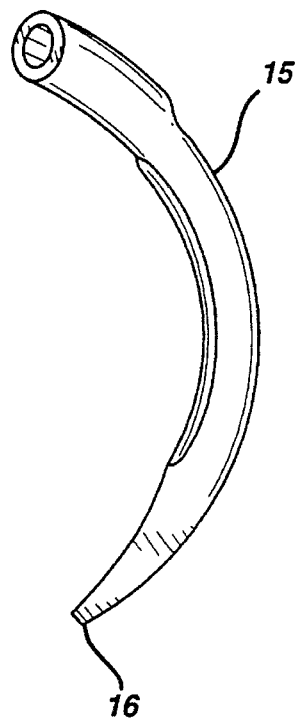
FIG. 5 is a perspective view of a taper point needle having a semi-finished truncated point.

A flow diagram of the process of the present invention is seen in FIG. 1. Taper point needles 10 having conventional sharp piercing distal points 11, or semi-finished, truncated taper needle blanks 15 having truncated tips 16, (see FIGS. 4 and 5) are loaded into grinding apparatus 20. The taper point needles 10 having sharp piercing points 11 may be manufactured by any conventional manufacturing process including the taper point manufacturing process previously mentioned above. The semi-finished, truncated needle blanks 15 having truncated ends 16 are manufactured by using a similar process to the taper point needle process with the exception that a secondary series of grinding operations are eliminated and the first series of grinding operations are adjusted to make the desired finished taper.

Figure 6:
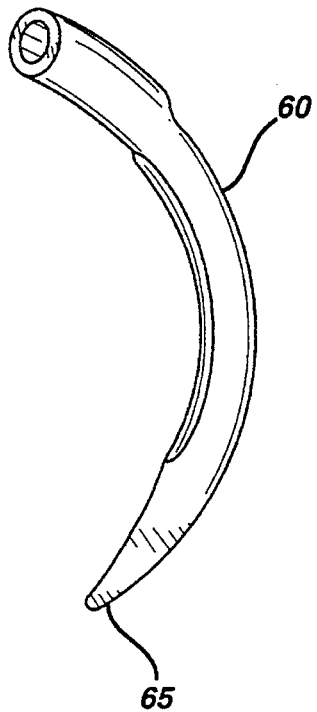
FIG. 6 is a perspective view of the taper point needle of FIG. 4 or the truncated needle blank of FIG. 5 after having been processed through the process of the present invention; the needle is seen to have a blunt tip.
Figure 6:
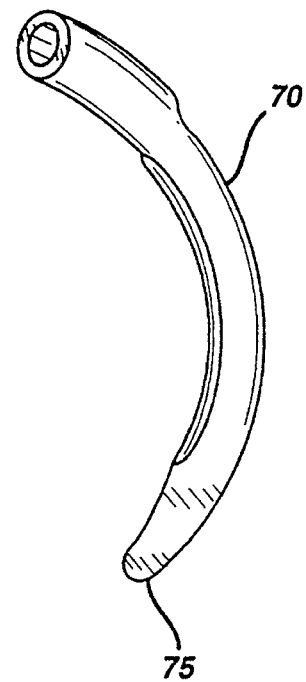

As illustrated in FIG. 1, the apparatus 20 is seen to contain abrasive media 40. Needles 10, or blanks 15, are charged to the apparatus 20. The apparatus 20 is mechanically displaced, e.g., rotated, vibrated, etc., such that needles 10 (or blanks 15) are contacted with the abrasive media 40 for a sufficient length of time to effectively produce blunt tip needles 60 (see FIG. 6). Typically, the processing or contact time may be about 1 to about 120 minutes, more typically about 5 to about 90 minutes, and preferably about 15 to about 60 minutes. It will be appreciated by those skilled in the art that the processing or contact time will depend upon a number of parameters including the needle size, the taper ratio, the media size and type, the size and configuration of the grinding apparatus, etc. When contacting the needles and abrasive media in the grinding apparatus, it is desirable to subject the needles to a "g" force sufficient to provide effective contact. The "g" force may typically range from about 1 to about 21, more typically about 10 to about 20, and preferably about 15 to about 17. A conventional blunt tip needle 70 having a conventional blunt tip 75 is seen in FIG. 7. The tip 75 is seen to have a larger radius or degree of bluntness. If desired, although not preferred, conventional blunt tip needles 70 having conventional blunt tips 75 can also be produced by the process of the present invention if desired.

Although not required, it is preferred to add sufficient amounts of processing aids 80 to the apparatus 20 to effectively assist in grinding or metal removal. The processing aids include those conventional in the art such as water, aluminum oxide powder, silicon carbide, polymers and the like. It will be appreciated that the amounts of processing aids utilized will vary with several parameters including the type and size of needles, the type and size of abrasive media, the type and size of grinding apparatus, the desired blunt tip profile, the amount of metal which must be removed to produce the profile, the processing time, the "g" force, etc.

The grinding apparatuses 20 which can be used in the practice of the present invention include conventional grinding apparatuses such as ball mills, barrel tumbling mills, vibratory mixing apparatuses, orbital mixing apparatuses, and the like and equivalents thereof. It is particularly preferred to use orbital mixing apparatuses 100 such as that illustrated in FIG. 2. Apparatus 100 is seen to consist of multiple (e.g., six) rotating cylinders 110 containing needles 10, media 40, and processing aid 80 mounted to a counter-rotating, orbitally mounted plate 120. The apparatuses 20 will typically consist of a vessel for receiving the abrasive media and needles, and a mechanism for displacing the vessel. The vessel will be capable of displacement, preferably rotation, in a manner effective to provide sufficient contact between the needles and abrasive media. The vessel may be open during grinding, e.g., when using an apparatus such as an orbital mixing apparatus, or sealed during grinding, e.g., when using an apparatus such as a ball mill.

The abrasive media which can be used in the practice of the present invention include any media sufficient to effectively produce a blunt tip on taper point surgical needles (or truncated taper needle blanks) when the needles and media are tumbled in a grinding apparatus. Examples of abrasive media which can be used include aluminum oxide, flint stone, porcelain, quartz, metals, alloys, ceramics and the like and equivalents thereof.

The size of the grinding media will be effective to sufficiently convert a taper point piercing tip to a blunt tip. The grinding media, i.e., the members collectively making up the grinding media, may have any effective configuration including conventional configurations such as triangles, cylinders, cones, stars, spheres and the like and equivalents thereof and combinations thereof. It is particularly preferred to use grinding media having a triangular or cylindrical configuration as illustrated in FIGS. 3A, 3B and 3C. The size of the grinding media for a cubic triangular configuration as seen in FIG. 3A may typically be about 1"×1"×1" by ¼" thick to about 0.5"×0.5"×0.5" by ⅛" thick. The size of the grinding media for a cylindrical configuration seen in FIG. 3B may typically be about 1/16" radius×¼" length to about ¼" radius by ½" length. The size of the grinding media for the elongated member having a triangular cross-section and rounded corners as illustrated in FIG. 3C may typically be about ⅛"×⅛"×⅛"×0.75".

The needles 60 of the present invention may be made from conventional materials including martensitic or austenitic stainless steels, plastics, composites, laminates, Nitinol and the like and equivalents thereof. It is particularly preferred to use Type 420 stainless steel.

The needles 60 manufactured by the process of the present invention will have a distal blunt tip 65 which will have a configuration which will typically vary in accordance with grinding time, e.g., a smaller radius with shorter processing times and a larger radius with longer processing times, although other factors may affect the grinding time necessary to achieve a desired radius as mentioned herein including metal type, media type, etc. The blunt tip 65 when ground for a shorter time may, for example, have a radius of about 0.002" to about 0.10", while the tip 65 when ground for a longer time may have a radius of about 0.010" to about 0.018". Of course, a variety of needle radii can be produced by the process of the present invention and the radius will also depend upon the type and size of needles used to manufacture the blunt tip needles 60, the degree of sharpness of the needle tips, etc. The radius of the blunt tip 65 will vary in accordance with several process parameters, as mentioned previously, including material of construction, type of grinding apparatus, needle wire size, grinding aids, "g" forces, grinding time, etc. Those skilled in the art will further appreciate that the process of the present invention can be used to produce needles 60 having a substantially flat tip 65 with substantially no radius.

The following example is illustrative of the principles and practice of the present invention although not limited thereto.

EXAMPLE

Figure 2:
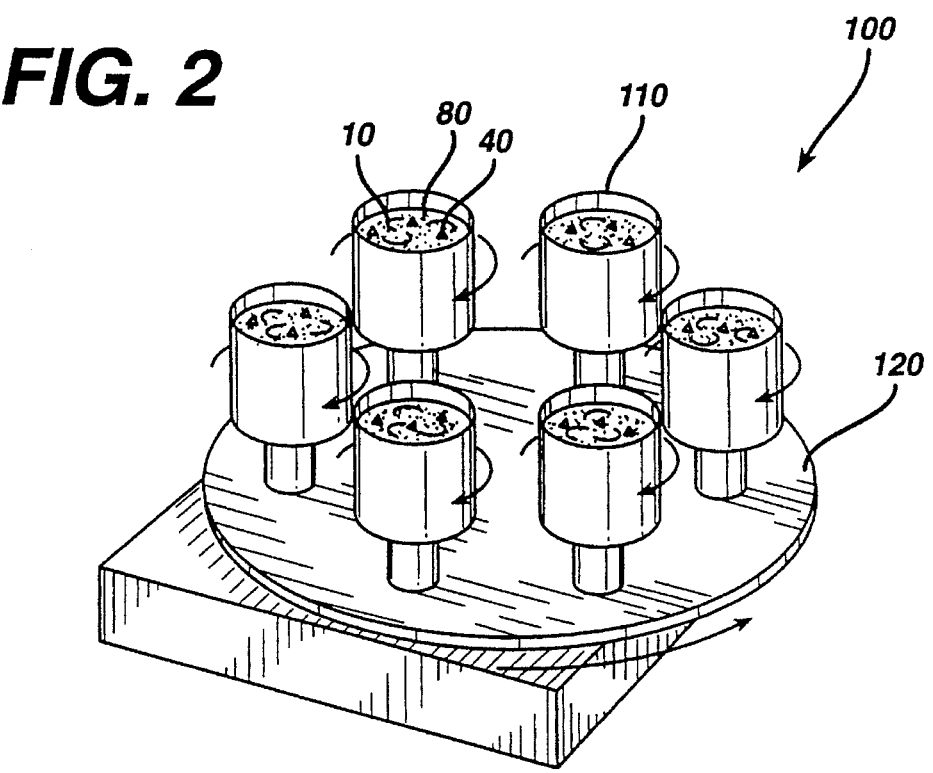
FIG. 2 is a perspective view of a process apparatus useful in the process of the present invention.

A lot of about 3,000 taper point surgical needles having pointed piercing tips was loaded into an orbital grinding/mixing grinding apparatus 100 as illustrated in FIG. 2 having six barrels 110. The barrels 110 contained an abrasive media 40 as illustrated in FIG. 3C. The following types and amounts of processing aids 80 were charged to each barrel 110 of the apparatus 100: water (about 1.0 liters) and aluminum oxide (about 5.6 kilograms). The apparatus 100 was manufactured by Harper, Inc., of Meriden, Conn. The needles 10 had a wire size of 0.39" and a length of about 1.500". The needles 10 were made from Type 420 stainless steel alloy. The needles 10 had conventional taper point piercing tips 11. The abrasive media 40, having a triangular cross-section as seen in FIG. 3C, consisted of abrasive porcelain members loaded up to 50% by volume of the apparatus 100's capacity. The size of the media 40 was about ⅛"×⅛"×⅛"×0.75". The grinding apparatus 100, as mentioned previously, consisted of six tumbling barrels 110 mounted on an orbital drive 120. The apparatus 100 functioned in the following manner: the six barrels 110 containing processing aids 80, abrasive media 40 and needles 10 were rotated in a clockwise direction while orbiting a central drive shaft in a counterclockwise direction to provide an average "g" force of about 16.0.

The needles 10 were processed in the apparatus for about 30 minutes, sufficient to contact the grinding media 40 with the needles 10 to effectively produce blunt tip needles 60 having the desired profile (i.e., tip 65). The profile produced can be described as a tip radius of about 0.006" to about 0.008". The needles 60 were then removed from the apparatus 100 and separated from the grinding media 40 by a combination of mechanical and magnetic screening. Inspection of the needles 60 revealed that the sharp taper point piercing tips 11 had been converted to blunt tips 65 having a radius of about 0.006" to about 0.008". The radii of the needles 60 varied as illustrated in the Table.

TABLE

| TIP RADIUS ANALYSIS | |
| --- | --- |
| DATA PTS. | = 75 |
| MEAN RADIUS | = .0045" |
| MIN VALUE | = .00381" |
| MAX VALUE | = .0060" |
| PREDICTED OUT OF SPEC VALUES | = 0 |
| CPK INDEX | = 1.97 |
| CP INDEX | = 2.36 |

The process of the present invention for manufacturing blunt tip surgical needles is seen to have numerous advantages when compared with the processes of the prior art. The process does not utilize cutting tools to produce blunt tips, accordingly, the process is not sensitive to set-up variations. Typically, in a conventional process, the manufacturing machines must be adjusted for different needle radii, raw materials and cutting tools. The process is also independent of the configuration of the taper point. It is possible to used needles with damaged points and convert them into useable blunt tip needles. The process is independent of the types of alloys from which the needles are made. Another advantage of the present process is that blunt tips having smaller radii can consistently be produced with minimal dimensional variability when compared to conventional manufacturing processes.

Although this invention has been shown and described with respect to detailed embodiments thereof, it will understood by those skilled in the art that various changes in form and detail thereof may be made without departing from the spirit and scope of the claimed invention.

We claim:

1. A method of manufacturing a surgical needle having a blunt tip, comprising:

placing at least one taper point surgical needle having a pointed piercing tip into an abrasive media; and, contacting the needle with the abrasive media for a sufficient amount of time and thereby abrading the needle to effectively convert the pointed piercing tip into a blunt tip.

2. The method of claim 1 wherein the abrasive media comprises ceramic members.

3. The method of claim 2 wherein the ceramic members have a triangular shape.

4. The method of claim 2 wherein the ceramic members have a cylindrical shape.

5. The method of claim 2 wherein the ceramic members have a triangular cross-section.

6. The method of claim 1 wherein the abrasive media additionally comprises a grinding aid.

7. The method of claim 1 wherein the blunt tip has a radius.

8. The method of claim 1 wherein the needles are subjected to a "g" force of from about 1 to about 21.

9. A method of manufacturing a surgical needle having a blunt tip, comprising:

placing at least one taper point surgical needle having a pointed piercing tip into a vessel containing an abrasive media;

displacing the vessel with respect to the needles and media thereby causing the needles to contact the abrasive media; and, maintaining the needles in the abrasive media in the vessel while the vessel is being displaced for a sufficient amount of time and thereby abrading the needles to effectively convert the pointed tip into a blunt tip.

10. The method of claim 9 wherein the abrasive media comprises ceramic members.

11. The method of claim 10 wherein the ceramic members have a triangular shape.

12. The method of claim 10 wherein the ceramic members have a cylindrical shape.

13. The method of claim 10 wherein the ceramic members have a triangular cross-section.

14. The method of claim 9 wherein the needles are subjected to a "g" force of from about 1 to about 21.

15. The method of claim 9 wherein the abrasive media additionally comprises a grinding aid.

16. The method of claim 9 wherein the blunt tip has a radius.

17. The method of claim 9 wherein the vessel is displaced by rotation.

18. A method of manufacturing a surgical needle having a blunt tip, comprising:

placing at least one truncated tapered needle blank having a truncated end tip into an abrasive media; and, contacting the blank with the abrasive media for a sufficient amount of time and thereby abrading the needle blank to effectively convert the truncated end tip into a blunt tip.

19. The method of claim 18 wherein the abrasive media comprises ceramic members.

20. The method of claim 19 wherein the ceramic members have a triangular shape.

21. The method of claim 19 wherein the ceramic members have a cylindrical shape.

22. The method of claim 19 wherein the ceramic members have a triangular cross-section.

23. The method of claim 18 wherein the needles are subjected to a "g" force of from about 1 to about 21.

24. The method of claim 18 wherein the abrasive media additionally comprises a grinding aid.

25. The method of claim 18 wherein the blunt tip has a radius.

26. A method of manufacturing a surgical needle having a blunt tip, comprising:

placing at least one truncated tapered needle blank having a truncated end tip into a vessel containing an abrasive media wherein the vessel comprises means for displacing the vessel;

displacing the vessel with respect to the media and blanks thereby causing the blanks to contact the abrasive media; and, maintaining the blanks in the abrasive media while the vessel is being displaced for a sufficient amount of time and thereby abrading the blanks to effectively convert the truncated tip of each blank into a blunt tip.

27. The method of claim 26 wherein the abrasive media comprises ceramic members.

28. The method of claim 27 wherein the ceramic members have a triangular shape.

29. The method of claim 27 wherein the ceramic members have a cylindrical shape.

30. The method of claim 27 wherein the ceramic members have a triangular cross-section.

31. The method of claim 26 wherein the needles are subjected to a "g" force of from about 1 to about 21.

32. The method of claim 26 wherein the abrasive media additionally comprises a grinding aid.

33. The method of claim 26 wherein the blunt tip has a radius.

34. The method of claim 26 wherein the vessel is displaced by rotation.

* * * * *